United States Patent
Kinoshita et al.

(10) Patent No.: US 7,968,290 B2
(45) Date of Patent: Jun. 28, 2011

(54) METHOD OF DETECTING GENE

(75) Inventors: Kenji Kinoshita, Hyogo (JP); Kazuhiko Fujiwara, Tokyo (JP); Kanehisa Yokoyama, Tokyo (JP); Kentaro Fujimoto, Tokyo (JP); Toru Yakabe, Tokyo (JP)

(73) Assignee: Sumitomo Bakelite Co., Ltd., Tokyo (JP)

( * ) Notice: Subject to any disclaimer, the term of this patent is extended or adjusted under 35 U.S.C. 154(b) by 555 days.

(21) Appl. No.: 11/920,559

(22) PCT Filed: May 16, 2006

(86) PCT No.: PCT/JP2006/309725
§ 371 (c)(1), (2), (4) Date: Nov. 16, 2007

(87) PCT Pub. No.: WO2006/123647
PCT Pub. Date: Nov. 23, 2006

(65) Prior Publication Data
US 2009/0042190 A1    Feb. 12, 2009

(30) Foreign Application Priority Data
May 17, 2005    (JP) .................................. 2005-144108

(51) Int. Cl.
*C12Q 1/68* (2006.01)
*C12Q 1/26* (2006.01)
*C12Q 1/28* (2006.01)
*C12P 19/34* (2006.01)
*C07H 21/02* (2006.01)
*C07H 21/04* (2006.01)

(52) U.S. Cl. ............... 435/6; 435/91.1; 435/25; 435/28; 536/23.1; 536/24.33

(58) Field of Classification Search .................. None
See application file for complete search history.

(56) References Cited

U.S. PATENT DOCUMENTS
2001/0036632 A1    11/2001    Yu et al.
2004/0035787 A1    2/2004    Tanga et al.
2004/0171040 A1*   9/2004    Bodepudi et al. ............. 435/6

FOREIGN PATENT DOCUMENTS

| | | |
|---|---|---|
| EP | 1 820 857 A1 | 8/2007 |
| GB | 2 422 335 A | 7/2006 |
| JP | 2004-154008 | 6/2004 |
| JP | 2004-184143 | 7/2004 |
| JP | 2004-198402 | 7/2004 |
| JP | 2005-30913 | 2/2005 |
| JP | 2006-17458 | 1/2006 |
| JP | 2006-71309 | 3/2006 |
| JP | 2006-174788 | 7/2006 |
| JP | 2006-176720 | 7/2006 |
| JP | 2006-177745 | 7/2006 |
| WO | 2005/029095 A1 | 3/2005 |

OTHER PUBLICATIONS

Wen et al. A visual DNA chip for simultaneous detection of hepatitis B virus, hepatitis C virus and human immunodeficiency virus type-1. Biosensors and Bioelectronics 19:685-692 (2004).*

Tominaga et al. Colorimetric ELISA measurement of specific mRNA on immobilized-oligonucleotide-coated microtiter plates by reverse transcription with biotinylated mononucleotides. Clinical Chemistry 42(11):1750-1757 (1996).*

Adessi C. et al., "Solid phase DNA amplification: characterization of primer attachment and amplification mechanisms", Nucleic Acids Res. 2000, vol. 28, No. 20, e87.

Supplementary European Search Report for Application No. EP 06 746 439.6.

Park J. et al., Evaluation of 2-methacryloyloxyethyl phosphoricholine polymeric nanoparticle for immunoassay of C-reactiive protein detection., Anal. Chem., 2004, vol. 76, No. 9, pp. 2649-2655.

* cited by examiner

*Primary Examiner* — Samuel C Woolwine
(74) *Attorney, Agent, or Firm* — Smith, Gambrell & Russell, LLP

(57) ABSTRACT

A method of detecting a gene including immobilizing a primer for DNA elongation onto an insoluble carrier having on the surface thereof a polymer substance containing a first unit having a phosphorylcholine group and a second unit having a carboxylic acid-derived group having an electron-attractive substituent bound to a carbonyl group; annealing the template DNA fragments or RNA fragments with the primer for DNA elongation, so as to elongate the DNA primer while incorporating therein an enzyme, thereby allowing coloration of a chromogenic reagent by its enzymatic action; and judging whether the DNA fragments or RNA fragments of the gene presents or not, based on the degree of coloration.

11 Claims, No Drawings

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial
<220> FEATURE:
<223> OTHER INFORMATION: Designed origonucleotide based on beta-actin
      gene

<400> SEQUENCE: 1
actcccggat tgcgc                                                    15
```

```
<210> SEQ ID NO 2
<211> LENGTH: 20
<212> TYPE: DNA
<213> ORGANISM: Artificial
<220> FEATURE:
<223> OTHER INFORMATION: Designed origonucleotide based on beta-actin
      gene

<400> SEQUENCE: 2
aaactcccgg attgcgctcc                                              20

<210> SEQ ID NO 3
<211> LENGTH: 25
<212> TYPE: DNA
<213> ORGANISM: Artificial
<220> FEATURE:
<223> OTHER INFORMATION: Designed origonucleotide based on beta-actin
      gene

<400> SEQUENCE: 3
tgtaaactcc cggattgcgc tccct                                        25

<210> SEQ ID NO 4
<211> LENGTH: 50
<212> TYPE: DNA
<213> ORGANISM: Artificial
<220> FEATURE:
<223> OTHER INFORMATION: Designed origonucleotide based on beta-actin
      gene

<400> SEQUENCE: 4
aaggcgggag ggagcgcaat ccgggagttt acaaatggac aaacttctat             50
```

METHOD OF DETECTING GENE

TECHNICAL FIELD

The present invention relates to a method of detecting a gene by immobilizing a primer DNA chain to the surface of a predetermined carrier, and allowing a DNA chain to elongate while using a DNA fragment or an RNA fragment of a gene as a template.

BACKGROUND ART

Detection and diagnosis using gene, such as inspecting expression of genes, and identification of bacteria and viruses, are routine procedures in the field of biochemistry. Conventional detection of gene has relied upon electrophoretic method, whereas a method having recently been applied is such as inspecting a plurality of genes at a time using a DNA microarray.

The conventional electrophoretic method takes a longer time before the detection, due to PCR reaction and electrophoresis, wherein procedures of the electrophoresis is labor-consuming.

Gene detection with the aid of microarray has need of using an expensive phosphorescent reagent, and has need of a microarray-dedicated expensive detector, so that such a method has been adopted only to a limited degree in the fields of clinical inspection, food inspection and so forth.

Aiming at solving this problem, Patent Document 1 discloses a method of detecting a gene based on visualization. The method described in this Patent Document is such as amplifying a gene by the LAMP process, and achieving visualization using an intercalator such as SYBR Green I, allowing judgment of presence/absence of a target gene to be detected, but is incapable of quantifying the gene present in a sample.

[Patent Document 1] Japanese Laid-Open Patent Publication No. 2004-154008

DISCLOSURE OF THE INVENTION

It is therefore an object of the present invention to provide a method of detecting a gene, being simple to operate, allowing measurement in the visible light region, and adapted to quantification.

The present inventors have reached the present invention by adopting a method of elongating DNA on a carrier having a predetermined polymer substance on the surface thereof.

According to the present invention, there is provided (1) a method of detecting a gene using an insoluble carrier having on the surface thereof a polymer substance containing a first unit having a phosphorylcholine group and a second unit having a carboxylic acid-derived group having an electron-attractive substituent bound to a carbonyl group, including:

(a) preparing a primer-immobilized carrier by immobilizing a primer for DNA elongation onto the surface of the carrier;

(b) adding, onto the primer-immobilized carrier, a DNA fragment or RNA fragment of a gene to be detected, optionally heated up to the thermal denaturation temperature of the DNA chain; a DNA polymerase, RNA polymerase or reverse transcriptase; and nucleotide monomers (dATP, dCTP, dGTP, dUTP);

(c) carrying out annealing at a predetermined temperature so as to hybridize the DNA fragment or the RNA fragment, with the primer for DNA elongation;

(d) forming a DNA chain by elongating the primer for DNA elongation; and (e) removing a liquid phase used in steps (b) to (d), if necessary, wherein thus-elongated DNA chain is introduced with an enzyme capable of allowing a chromogenic reagent to develop color, allowing judgment of presence of the DNA fragment or RNA fragment of the gene, based on the degree of coloration;

(2) the method of detecting a gene of (1), further including, for the case where step (b) is carried out without heating up to the thermal denaturation temperature of the DNA chain, before step (c), elevating temperature of the reaction system containing the individual materials introduced in step (b), up to the thermal denaturation temperature of the DNA chain;

(3) the method of detecting a gene of (1), wherein, in step (b), the DNA fragment or RNA fragment of a gene to be detected is added onto the primer-immobilized carrier, after being heated up to the thermal denaturation temperature of the DNA chain;

(4) the method of detecting a gene of (1), wherein, in step (b), the DNA fragment or RNA fragment of a gene to be detected; the DNA polymerase, RNA polymerase or reverse transcriptase; and the nucleotide monomers are added onto the primer-immobilized carrier, after being heated up to the thermal denaturation temperature of the DNA chain;

(5) the method of detecting a gene of (1), wherein, in step (b), any of the nucleotide monomers is labeled with an enzyme capable of allowing a chromogenic reagent to develop color, and thereby the enzyme is introduced into the elongated DNA chain;

(6) the method of detecting a gene of (1), wherein, in step (b), any of the nucleotide monomers is labeled with biotin, and after step(e), a solution containing streptoavidin labeled with an enzyme capable of allowing a chromogenic reagent to develop color is added, and thereby the enzyme is introduced into the elongated DNA chain;

(7) the method of detecting a gene of (1) to (6), wherein step enzyme labeled on the elongated DNA chain is an oxidase or a reductase;

(8) the method of detecting a gene of (1) to (6), wherein the enzyme labeled on the elongated DNA chain is either of peroxidase or alkali phosphatase;

(9) the method of detecting a gene of (1) to (8), wherein step (d) is carried out while adjusting the temperature to a predetermined value between annealing temperature and thermal denaturation temperature;

(10) the method of detecting a gene of (1) to (9), wherein, in step (a), the primer is immobilized to the surface of the carrier, through a covalent bond formed with a site of a carboxylic acid-derived group;

(11) the method of detecting a gene of (1) to (10), wherein the polymer substance further contains a third unit having a butyl methacrylate group;

(12) the method of detecting a gene of (1) to (11), wherein the carrier contains, in addition to the polymer substance, a second polymer substance containing a first unit having a phosphorylcholine group, and a third unit having a butyl methacrylate group;

(13) the method of detecting a gene of (1) to (12), wherein the carrier is composed of a plastic material;

(14) the method of detecting a gene of (1) to (13), wherein a colored dye adsorbs to the elongated DNA chain, allowing measurement of the degree of adsorption of the dye as color density; and

(15) the method of detecting a gene of (1) to (13), wherein the degree of coloration is measured based on absorption.

According to the present invention, gene may be detected by simple operations within a short time, may be detected in the visible light region, and may not only be judged in terms of presence/absence thereof, but also be quantified.

BEST MODES FOR CARRYING OUT INVENTION

Embodiments of the present invention will be detailed below.

The method of detecting a gene according to the present invention is a method of detecting a gene using an insoluble carrier having on the surface thereof a polymer substance containing a first unit having a phosphorylcholine group and a second unit having a carboxylic acid-derived group having an electron-attractive substituent bound to a carbonyl group, including:

(a) preparing a primer-immobilized carrier by immobilizing a primer for DNA elongation onto the surface of the carrier;

(b) adding, onto the primer-immobilized carrier, a DNA fragment or RNA fragment of a gene to be detected optionally heated up to the temperature up to the thermal denaturation temperature of the DNA chain; a DNA polymerase, RNA polymerase or reverse transcriptase; and nucleotide monomers (dATP, dCTP, dGTP, dUTP);

(c) carrying out annealing at a predetermined temperature so as to hybridize the DNA fragment or the RNA fragment, with the primer for DNA elongation;

(d) forming a DNA chain by elongating the primer for DNA elongation; and (e) removing a liquid phase used in (b) to (d), if necessary, wherein thus-elongated DNA chain is introduced with an enzyme capable of allowing a chromogenic reagent to develop color, allowing judgment of presence of the DNA fragment or RNA fragment of the gene, based on the degree of coloration.

In other words, a primer for DNA elongation is immobilized onto the surface of the carrier which has on the surface thereof a polymer substance containing a first unit having a phosphorylcholine group and a second unit having a carboxylic acid-derived group having an electron-attractive substituent bound to a carbonyl group, DNA is allowed to elongate using a DNA fragment or RNA fragment in a sample as a template, with the aid of an enzyme having reverse transcriptase and/or polymerase activity, wherein an oxidase or reductase is introduced therein in the process of elongation, so as to allow the chromogenic substrate to develop color, to thereby enable judgment of existence and quantification of a target DNA or RNA sequence to be detected in a sample, in the visible light region.

In step (a), a primer for DNA elongation is immobilized onto the surface of the carrier, to thereby prepare a primer-immobilized carrier.

The carrier used in the present invention is configured as having, on the surface thereof, a polymer substance containing a first unit having a phosphorylcholine group and a second unit having a carboxylic acid-derived group having an electron-attractive substituent bound to a carbonyl group.

The polymer substance containing a first unit having a phosphorylcholine group and a second unit having a carboxylic acid-derived group having an electron-attractive substituent bound to a carbonyl group is a polymer having both properties of suppressing non-specific absorption of a DNA chain and RNA chain, and of immobilizing a DNA chain. In particular, the phosphorylcholine group contained in the first unit plays a role of suppressing non-specific absorption of a template RNA fragment, and the carboxylic acid-derived group contained in the second unit plays a role of chemically immobilizing the primer. In short, the primer is immobilized onto the surface of the carrier, through a covalent bond at the site of the carboxylic acid-derived group contained in the second unit.

The first unit typically has a (meth)acryloyloxyalkyl phosphorylcholine group such as 2-methacryloyloxyethyl phosphorylcholine group, or 6-methacryloyloxyhexyl phosphorylcholine group;

a (meth) acryloyloxyalkoxyalkyl phosphorylcholine group such as 2-methacryloyloxyethoxyethyl phosphorylcholine group or 10-methacryloyloxyethoxynonyl phosphorylcholine group; and an alkenyl phosphorylcholine group such as allyl phosphorylcholine group, butenyl phosphorylcholine group, hexenyl phosphorylcholine group, octenyl phosphorylcholine group, or decenyl phosphorylcholine group, allowing a configuration having the phosphorylcholine group to be contained in these groups.

Of these groups, 2-methacryloyloxyethyl phosphorylcholine is preferable. By adopting a configuration in which the first unit has a 2-methacryloyloxyethyl phosphorylcholine, non-specific absorption of template RNA fragments onto the surface of the carrier may more reliably be suppressed.

The carboxylic acid derivative is an activated form of carboxyl group of carboxylic acid, and is a carboxylic acid having a leaving group bonded via C=O. More specifically, the carboxylic acid derivative is an activated compound having, as being bound to a carbonyl group, a group more electron-attractive than alkoxyl groups, and thereby being made more labile to nucleophilic reaction. The carboxylic acid derivative is a compound showing reactivity to amino group, thiol group, hydroxyl group and so forth.

The activated carboxylic acid derivative may further specifically be exemplified by compounds obtained by modifying carboxyl group of carboxylic acid, such as acrylic acid, methacrylica acid, crotonic acid, maleic acid, and fumaric acid, into acid anhydride, acid halide, activated ester and activated amide. The carboxylic acid-derived group is an activated group derived from these compounds, and may typically has an activated ester group such as p-nitrophenyl group and N-hydroxysuccinimide group; and halogens such as —Cl and —F.

The carboxylic acid-derived group may be a group expressed by the formula (1) below:

(Chemical Formula 1)

(where in the formula (1), "A" represents a leaving group excluding hydroxyl group).

A monovalent group shown in the formula (1) may be either one of groups expressed by the formulae (p) and (q) below:

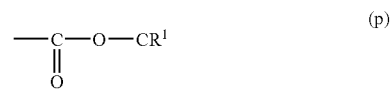

-continued

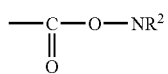
(q)

(where in the formula (p) and the formula (q), each of $R^1$ and $R^2$ independently represents a monovalent organic group which may be straight-chain-like, branched or cyclic. In the formula (p), $R^1$ may be a divalent group capable of forming a ring together with C. In the formula (q), $R^2$ may be a divalent group capable of forming a ring together with N).

The group expressed by the formula (p) may be exemplified by the groups typically shown by the formulae (r), (s) and (w) below. The group expressed by the formula (q) may be exemplified by the group typically shown by the formula (u) below.

The group expressed by the formula (1) may be groups derived from acid anhydride typically expressed by the formula (r) and formula (s) below;

groups derived from acid halide expressed by the formula (t) below;

groups derived from activated ester expressed by the formula (u) and formula (w) below; and groups derived from activated amide expressed by the formula (v) below;

(Chemical Formula 3)

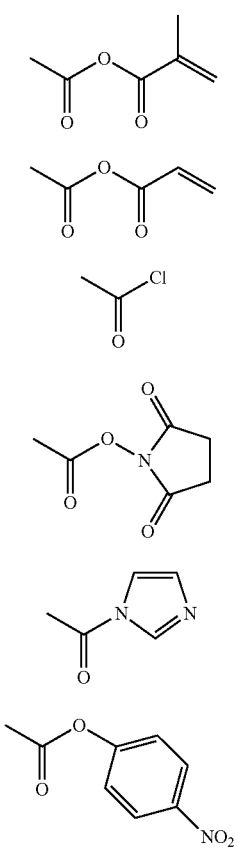

Of the carboxylic acid-derived groups, the activated ester groups may preferably be used by virtue of their excellent reactivity under mild conditions. The mild conditions may be neutral or alkali conditions, more specifically those with pH7.0 or higher and 10.0 or lower, still more specifically pH7.6 or higher and 9.0 or lower, and furthermore specifically pH8.0.

The "activated ester group" specified in this patent specification is not strictly defined, but is generally used as an idiomatic technical expression in the fields of various chemical syntheses such as polymer chemistry, peptide synthesis and so forth, as indicating a category of esters having, on the alcohol side of the ester group thereof, a highly-acidic, electron-attractive group and thereby making the compound more labile to nucleophilic reaction, in other words, highly-reactive ester groups. In the field of peptide synthesis, the active ester process is used as one method of activating the C-terminal of amino acids or peptides, as described in "Pepuchido Gosei no Kiso to Jikken (Basics and Experiments of Peptide Synthesis)", co-written by Nobuo IZUMIYA, Tetsuo KATO, Michihiko AOYAGI and Michinori Waki, 1985, published by Maruzen Co., Ltd.

In practice, it is an ester group having an electron-attractive group on the alcohol side of the ester group thereof, and thereby activated to a larger degree than alkyl esters. The activated ester group has reactivity to groups such as amino group, thiol group, and hydroxyl group. More specifically, phenol esters, thiophenol esters, N-hydroxylamine esters, cyanomethyl esters, and esters of heterocyclic hydroxy compounds are known as activated ester groups having far higher activities than those of alkyl esters.

Now the description will be made on the case where the activated carboxylic acid derivative group in the polymer substance is the activated ester group. The activated ester group is exemplified, for example, by p-nitrophenyl group, N-hydroxysuccimide group, succinimide group, phthalimide group, and 5-norbornene-2,3-dicarboxylmide group, wherein p-nitrophenyl group is preferably used.

As for the carrier to have primers immobilized thereon, specific combinations of the first unit and the second unit may be such that the first unit having a phosphorylcholine group has a 2-methacryloyloxyethyl phosphorylcholine group, and the activated ester group is p-nitrophenyl group.

The polymer substance used for a coating layer of the carrier of this embodiment may contain any group other than the phosphorylcholine group and the carboxylic acid-derived group. The polymer substance may also be a copolymer. More specifically, the polymer substance is preferably a copolymer containing butyl methacrylate groups. This configuration can make the polymer substance hydrophobic to an appropriate degree, and can thereby ensure a more preferable level of adsorptivity of the polymer substance to the surface of the carrier.

More specifically, the polymer substance may be configured by a copolymer composed of a first monomer having 2-methacryloyloxyethyl phosphorylcholine (MPC) group, a second monomer having a p-nitrophenyloxycarbonyl polyethylene glycol methacrylate (NPMA) group, and a third monomer having butyl methacrylate (BMA) group. A copolymer poly(MPC-co-BMA-co-NPMA) (PMBN) containing them is schematically expressed by the formula (2) below:

(Chemical Formula 4)

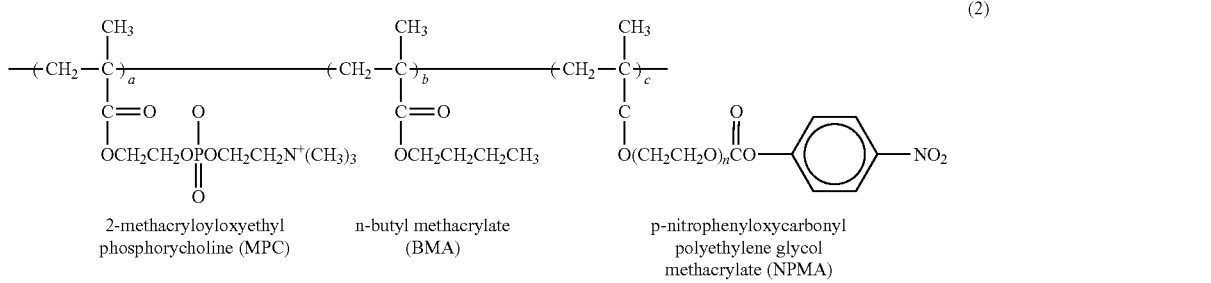

2-methacryloyloxyethyl phosphorycholine (MPC)   n-butyl methacrylate (BMA)   p-nitrophenyloxycarbonyl polyethylene glycol methacrylate (NPMA)

Copolymer composed of 2-methacryloyloxyphosphorylcholine, and n-butyl methacrylate, and p-nitrophenyloxy carbonyl polyethylene glycol methacrylate Where, in the formula (2), each of a, b and c independently represents a positive integer. In the formula (2), the first to third monomer may form a block copolymer, or these monomers may form a random copolymer.

Thus-configured copolymer expressed by the formula (2) is more excellently balanced among an appropriate degree of hydrophobicity, a property of suppressing non-specific adsorption of the template RNA fragment, and a property of immobilizing the primer. Therefore, by using such copolymer, the carrier may be covered with the polymer substance in a more reliable manner, and the primer may be introduced by immobilization through a covalent in a more reliable manner, while suppressing non-specific adsorption of the template RNA fragment to the carrier coated with the polymer substance.

The copolymer expressed by the formula (2) may be obtained by mixing the individual monomers of MPC, BMA, and NPMA, according to any publicly-known methods of polymerization such as radical polymerization. For the case where the copolymer expressed by the formula (2) is produced by radical polymerization, the polymerization may be proceeded by solution polymerization in an atmosphere of inert gas such as Ar, under temperature conditions of 30° C. or higher and 90° C. or lower.

The solvent used for solution polymerization may properly be selected from the group consisting of alcohols such as methanol, ethanol and isopropanol, ethers such as diethyl ether, and organic solvents such as chloroform, and the solvent(s) may be used singly or in combination. More specifically, a mixed solvent of diethyl ether and chloroform at a ratio by volume of 8:2 may be used.

A radical polymerization initiator used for the radical polymerization reaction may be any of those generally used. For example, azo-base initiators such as azobisisobutyronitrile (AIBN) and azobisvaleronitrile; and oil-soluble organic peroxides such as lauroyl peroxide, benzoyl peroxide, t-butylperoxy neodecanoate, and t-butylperoxy pivalate may be used.

More specifically, the polymerization may be proceeded by using a mixed solvent of diethyl ether and chloroform at a ratio by volume of 8:2 and AIBN, in Ar at 60° C. for 2 to 6 hours.

Although the embodiment has been explained referring to the case of using the polymer substance containing the third unit having a butyl methacrylate group, the polymer substance may contain a first polymer substance containing a first unit having a phosphorylcholine group and a second unit having a carboxylic acid-derived group, and may additionally contain a second polymer substance containing a first unit having a phosphorylcholine group and a third unit having a butyl methacrylate group.

The first unit of the first polymer substance and the first unit of the second polymer substance may have the same structure or different structures. For the case where the first polymer substance contains the third unit having a butyl methacrylate group, the third unit of the first polymer substance and the third unit of the second polymer substance may have the same structure or different structures.

The second polymer substance as described in the above may be used as a polymer for suppressing the non-specific adsorption of the template DNA fragment. As this sort of polymer, MPC polymer (from NOF Corporation), containing 30 mol % of phosphorylcholine group and 70 mol % of butyl methacrylate group, may typically be used.

For the case where the polymer substance is composed of the first polymer substance and the second polymer substance, these polymer substances may be mixed. Because each of the polymer substances is soluble, for example, in an ethanol solution, the mixed polymer may readily be obtained by mixing the individual polymer solutions.

The carrier containing, in the surficial portion thereof, the coat layer composed of any of the above-described polymer substances may be obtained by coating a liquid containing the polymer substances onto the surface of the carrier processed into a predetermined shape, and by drying. It is also allowable to immerse the carrier into a liquid containing the polymer substances, followed by drying.

Use of plastic materials for the carrier is preferable in view of ensuring flexibility in modification of shape and size, and possibility of provision at lower prices. From the viewpoints of readiness in the surface treatment and mass-productivity, thermoplastic resins may be used.

The thermoplastic resins are not specifically limited so far they have a certain level of heat resistance. As heat-resistant resins, straight-chain polyolefins such as polyethylene and polypropylene; cyclic polyolefins; and fluorine-containing resins may typically be used. Among these resins, saturated cyclic polyolefins are preferable for optical analyses, by virtue of their excellence particularly in heat resistance, chemical resistance, low phosphorescence, transparency and moldability, and may preferably be used as materials for composing the carrier.

The carrier containing, in the surficial portion thereof, any of the above-described plastic materials may be obtained by coating a liquid containing the polymer substances onto the surface of the carrier processed into a predetermined shape, and by drying. It is also allowable to immerse the carrier into a liquid containing the polymer substances, followed by drying.

For the case where the carrier is composed of any of the plastic materials, shape of the carrier is not limited to plate, but may be exemplified by those in a form of micro-titer plate represented by those of 96-well type or 384-well type, in a form of substrate represented by slide glass, in a form of bead, and in a form of sheet.

Next, a method of immobilizing the primer onto the surface of the carrier will be explained.

The primers may be immobilized onto the surface of the carrier, typically (i) by allowing at least a portion of activated ester groups, out of a plurality of activated ester groups contained in the polymer substance on the carrier, to react with the primers so as to form covalent bonds, to thereby immobilize the primers on the surface of the carrier, and then (ii) by inactivating the activated ester groups on the surface of the carrier, other than those having the primers immobilized thereon, that is, by inactivating the residual activated ester groups. The individual process steps will be explained below.

In the step (i), for the case where the carrier is in a form of substrate, and the primers to be annealed with the template RNA fragments are immobilized onto such substrate, a preferable method may be such as spotting a liquid containing the primers dissolved or dispersed therein. A portion of the activated ester groups contained in the polymer substance is reacted with the primers, thereby the covalent bonds are formed with the primers.

The liquid containing the primer dissolved or dispersed therein may be adjusted to neutral to alkaline, and typically to pH7.6 or above.

After the spotting, the carrier may be washed using pure water of a buffer solution, for the purpose of removing the primers not immobilized onto the surface of the carrier.

After the washing, the activated esters on the surface of the carrier, other than those having the primers immobilized thereon, are inactivated as shown in the step (ii), using an alkaline compound, or any compounds having a primary amino group.

As the alkali compound, sodium hydroxide, potassium hydroxide, sodium carbonate, sodium hydrogen carbonate, disodium hydrogen phosphate, calcium hydroxide, magnesium hydroxide, sodium borate, lithium hydroxide, potassium phosphate and so forth may be used.

As the compound having a primary amino group, glycine, 9-aminoaquadine, aminobutanol, 4-aminobutyric acid, aminocapric acid, aminoethanol, 5-amino 2,3-dihydro-1,4-pentanol, aminoethanethiol hydrochloride, aminoethanethiol sulfate, 2-(2-aminoethylamino)ethanol, 2-aminoethyl dihydrogen phosphate, aminoethyl hydrogen sulfate, 4-(2-aminoethyl)morpholine, 5-aminofluorescein, 6-aminohexanoic acid, aminohexylcellulose, p-aminohippuric acid, 2-amino-2-hydroxymethyl-1,3-propanediol, 5-aminoisophthalic acid, aminomethane, aminophenol, 2-aminooctane, 2-aminooctanoic acid, 1-amino-2-propanol, 3-amino-1-propanol, 3-aminopropene, 3-aminopropionitrile, aminopyridine, 11-aminoundecanoic acid, amino salicylic acid, aminoquinoline, 4-aminophthalonitrile, 3-aminophthalimide, p-aminopropiophenone, aminophenyl acetate, aminonaphthalene and so forth may be used. Of these, aminoethanol and glycine may preferably be used.

The primer to be immobilized onto the carrier preferably has an amino group primarily introduced thereinto, in view of enhancing reactivity with the activated ester group. The amino group is excellent in reactivity with the activated ester group, so that by using the primer having the amino group introduced thereinto, the primer may be immobilized onto the surface of the carrier in an effective and strong manner. Position of introduction of amino group may be on the terminal of the molecular chain of the primer, or may be on the side chain, wherein introduction on the terminal of the molecular chain may be preferable, in view of allowing annealing with a complementary template RNA fragment to proceed in a more efficient manner.

By these procedures, an array having the primers immobilized on the surface of the carrier may be obtained.

Next, in step (b), the primer-immobilized carrier is added with DNA fragments or RNA fragments of the gene to be detected, optionally heated up to the thermal denaturation temperature of the DNA chain, and DNA polymerase, RNA polymerase or reverse transcriptase, and nucleotide monomers (dATP, dCTP, dGTP, dUTP). The DNA fragments or RNA fragments to be added may preliminarily be heated, before the addition, up to the thermal denaturation temperature, and thereby the thermal denaturation of the DNA fragments or RNA fragments, which serves as the template for elongation reaction, may more reliably be proceeded, rather than by annealing described later. The sequential order of addition of these materials are not specifically limited, allowing addition at a time, wherein these materials in this case may be prepared as a sample separate from the system containing the primer-immobilized carrier, and may be added onto the primer-immobilized carrier, while being preheated up to the annealing temperature if necessary.

The sample containing the DNA fragments or RNA fragments, which serve as the template for amplifying DNA, to be annealed with the primers immobilized onto the surface of the carrier is introduced in this way, and further a solution containing dATP, dCTP, dGTP and dUTP as the nucleotide monomers is introduced.

In the reaction of thus-introduced sample, elongation reaction using the DNA or RNA template, with the aid of reverse transcriptase and/or the other enzyme(s) having polymerase activity, such as DNA polymerase, RNA polymerase is allowed to proceed.

Reverse transcriptase and/or the other enzymes having polymerase activities applicable to the present invention includes Moloney murine leukemia virus (M-MLV) reverse transcriptase, Rous sarcoma virus (RSV) reverse transcriptase, avian myeloblastosis virus (AMV) reverse transcriptase, Rous-associated virus (RAV) reverse transcriptase, myeloblastosis-associated virus (MAV) reverse transcriptase, human immunodeficiency virus (HIV) reverse transcriptase, retrovirus reverse transcriptase, retrotransposon reverse transcriptase, type B hepatitis reverse transcriptase, cauliflower mosaic virus reverse transcriptase, bacterial reverse transcriptase, *Thermus thermophilus* (Tth) DNA polymerase, *Thermus aquaticus* (Taq) DNA polymerase, *Thermotoga neopolitana* (Tne) DNA polymerase, *Thermotoga maritime* (Tma) DNA polymerase, *Thermococcus litoralis* (Tli, for example, VENT (registered trademark) brand) DNA polymerase, *Pyrococcus furiosus* (Pfu) DNA polymerase, *Pyrococus* species GBD (for example, DEEPVENT™ brand) DNA polymerase, *Pyrococcus woosii* (Pwo) DNA polymerase, *Bacillus sterothermophilus* (Bst) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus rubber* (Tru) DNA polymerase, *Thermus brockianus* (for example, DYNAZYME (registered trademark) brand) DNA polymerase, *Methanobacterium thermoautotrohicum* (Mth) DNA polymerase, variant, modified product and derivatives thereof, but are not limited thereto. Klenow fragment of DNA polymerase may be used. RNA polymerase may also be used.

When RNA is used as a template gene, it is more better to add RNase inhibitor, for the purpose of suppressing decomposition of the RNA.

Next, in step (b), for the case where preheating up to the thermal denaturation temperature of the DNA chain is not adopted, the temperature of the reaction system having the individual materials added onto the primer-immobilized carrier is elevated to a temperature not lower than the thermal denaturation temperature (melting temperature: Tm) of the DNA chain, for example up to 90° C. to 95° C. By this thermal denaturation, the DNA fragments, RNA fragments and primer, showing folded structures such as usually found in self-complementary chains, give straight-chain-like single strands. Such annealing is not necessary, when the materials to be added are preheated in step (b).

In step (c), the DNA fragments or the RNA fragments, and the primer for DNA elongation are hybridized by annealing at a predetermined temperature. More specifically, temperature of the reaction system is lowered to a temperature causing annealing of the primer and the template DNA fragments with each other (annealing temperature), typically to 4° C. to 65° C., and more preferably 45° C. to 65° C. By the annealing, the primer having a sequence complementary to a portion of the DNA fragments, and the DNA fragments are hybridized, to thereby give double strands.

In step (d), the primer for DNA elongation is elongated to produce a DNA chain. In the elongation reaction of DNA proceeded in this step, the temperature of the reaction system after the annealing is controlled to gradually elevate from the annealing temperature up to the thermal denaturation temperature. Alternatively, the temperature is adjusted to a predetermined temperature between the annealing temperature and the thermal denaturation temperature. In other words, the temperature of the reaction system is controlled to be the predetermined temperature between the annealing temperature and the thermal denaturation temperature, typically to 65° C. to 75° C. By controlling the temperature of the reaction system in this way, the elongation reaction of DNA proceeds.

Alternatively, thermal denaturation at a predetermined temperature may be proceeded, if necessary, after the elongation reaction of DNA chain in step (d), so as to make the DNA fragments or RNA fragments dissociate from the elongated DNA chain. More specifically, the reaction system after completion of the elongation reaction is kept at the thermal denaturation temperature of the DNA chain, typically at 90° C. to 95° C. By the thermal denaturation, the DNA fragments or the RNA fragments used as the template dissociate from the DNA double strands, leaving single-strand elongated DNA fragments on the surface of the carrier.

There are no special limitations on the reaction temperature and reaction time, allowing appropriate setting of reaction conditions, depending on characteristics of the DNA polymerase, restriction enzymes and so forth, and stability, quality and absolute content of the template DNA or RNA.

Next, in step (e), the liquid phase used in steps (b) to (d) is removed if necessary. More specifically, after completion of the elongation reaction, washing is carried out typically using a 0.1 wt % SDS solution, to thereby terminate the reaction for producing cDNA.

In this embodiment, the extended DNA chain has an enzyme incorporated therein, and by this enzyme the chromogenic reagent is allowed to develop color, making it possible to judge presence of the DNA fragments or RNA fragments of the gene, based on the degree of coloration. As a method of introducing the enzyme, any of the nucleotide monomers (dATP, dCTP, dGTP, dUTP) used in step (b) for DNA elongation are preliminarily labeled with the enzyme capable of allowing a chromogenic reagent to develop color, and the nucleotide monomers are added in step (b) so as to introduce the enzyme into the elongated DNA chain. The enzyme is however a protein, and a large molecular size thereof may interfere the DNA elongation, so that it is also allowable to preliminarily label any of the nucleotide monomers used in step (b) with biotin, and to add, after removal of the liquid phase in step (e), a solution containing streptoavidin labeled with an enzyme capable of allowing the chromogenic reagent to develop color, so as to introduce the enzyme into the elongated DNA chain. In other words, the biotin-labeled nucleotide monomers may be added, thereby introducing biotin into the DNA chain, and an enzyme-labeled streptoavidin solution may be added in the later step, so as to introduce the enzyme based on biotin-avidin interaction.

The enzyme capable of causing development of color of the chromogenic reagent labeled on the elongated DNA chain depends on what kind of compound is used for the chromogenic reagent, but may preferably be selected from oxidase or reductase, because many of the chromogenic reagents develop color through oxidation or reduction. It is also allowable to use peroxidases or alkali phosphatases, having conventionally been used as enzymes for chromogenic reagents, as the enzyme to be labeled on the elongated DNA chain. Use of these enzymes is preferable in view of easy availability of the chromogenic reagents.

The chromogenic reagent applicable herein may be NBT/BICP chromogenic reagent popularly used for coloration of membranes in the western blotting method, or may be TMBZ and OPD popularly used for coloration in the field of ELISA.

The degree of coloration ascribable to the chromogenic reagent depends on the amount of enzyme introduced into the elongated primer DNA chain, that is, the amount of elongated primer DNA chain. The colored dye adsorbs to the elongated DNA chain, and allows measurement of the degree of adsorption of dye in terms of color density. For example, the NBT/BICP chromogenic reagent adsorbs to elongated DNA or preliminarily-immobilized primer DNA chain, and shows the sites of spotting of the primer as being colored. Presence or absence of a target gene to be detected may be confirmed, by visually confirming the colored image. It is also possible to capture the colored image by an image scanner or a CCD camera, and to express the degree of coloration by numerical values using an image processing software (for example, NIH image), and to compare the amount of target gene to be detected.

The degree of coloration may be measured also by absorption, wherein use of a 96-well, micro-titer plate typically used for ELISA as the carrier allows measurement based on absorption, by using a micro-plate reader similarly to as in ELISA. In recent years, absorption spectrophotometers enabling measurement of absorption with a sample solution volume of 1 μl or around have commercially been available, with which the absorption may be measured using a carrier having fine fluid passageways or fine wells, and the amount of target gene to be detected may be compared.

EXAMPLES (Manufacturing of PMBN-Coated Substrate)

Using a saturated cyclic polyolefin resin (hydrogenated product of ring-opening polymer of 5-methyl-2-norbornene, MFR (melt flow rate): 21 g/10 minutes, rate of hydrogenation: substantially 100%, thermal deformation temperature=123° C.), a substrate was obtained in a glass-slide-like shape by injection molding. The substrate was immersed in a 0.5 wt % ethanol solution of 2-methacryloyloxyethyl phosphorylcholine-butyl methacrylate-p-nitrophenyloxy carbonyl polyethylene glycol methacrylate copolymer (poly(MPC-co-BMA-co-NPMA) (PMBN), ratio of the individual groups is 25:74:1 in terms of mol %) so as to introduce a polymer substance having phosphorylcholine groups and activated ester groups onto the surface of the substrate, to thereby obtain a plastic substrate (PMBN-coated substrate).

(Manufacture of Aldehyde Substrate)

Using a saturated cyclic polyolefin resin (hydrogenated product of ring-opening polymer of 5-methyl-2-norbornene, MFR: 21 g/10 minutes, rate of hydrogenation: substantially 100%, thermal deformation temperature=123° C.), a substrate was obtained in a glass-slide-like shape by injection molding. The mold was subjected to low-temperature oxygen plasma treatment so as to impart hydrophilicity to the surface. Next, a treatment solution for introducing amino group was prepared by dissolving γ-aminopropyl triethoxysilane as the amino alkylsilane into methanol to a concentration of 5% by weight, the substrate was immersed in the solution for 2 hours, taken out from the solution, then immersed in ultrapure water, allowed to stand, taken out, and dried. A glutaraldehyde solution was prepared by dissolving glutaraldehyde into PBS (−) to a concentration of 2% by weight, the aminoalkylsilane-treated substrate was immersed therein, allowed to stand for 4 hours, taken out, immersed in ultrapure water, washed, and dried. By these procedures, an aldehyde substrate having aldehyde groups on the surface thereof was obtained.

(Immobilization of Primer)

Each of a DNA primer (15 bases) having a sequence of ACTCCCGGATTGCGC (sequence No. 1), a DNA primer (20 bases) having a sequence of AAACTCCCGGATTGCGCTCC (sequence No. 2), and a DNA primer (25 bases) having a sequence of TGTAAACTCCCGGATTGCGCTCCCT (sequence No. 3), individually modified at the 5'-terminal with an amino group, was dissolved using a 0.25 M carbonate buffer (pH9.0), to thereby prepare a 10-μM DNA primer solution. Each solution was spotted, using a spotter (Marks-I from Hitachi Software Engineering Co., Ltd.) and a 100-μm-diameter cross cut pin, respectively onto the PMBN-coated substrate and the aldehyde substrate. Each substrate spotted with the oligo DNA was allowed to stand over a whole day and night in a closed container (10 cm×15 cm×3 cm) moistened inside with 200 μl of a 0.25 M phosphate buffer (pH8.5) so as to immobilize the primer. Thereafter, the individual substrates were subjected to blocking.

(Elongation Reaction of Primer DNA)

A solution of a 50-base template DNA fragment AAGGCGGGAGGGAGCGCAATCCGGGAGTTTACAAATGGACAAACTTCTAT (sequence No. 4) was prepared so as to adjust concentration of the template DNA fragment to 100 pM. Taq polymerase, and biotin-labeled dUTP, dATP, dCTP, dGTP were added to the template DNA solution, to thereby prepare a solution for DNA elongation reaction. The solution was supplied to the surface of the individual substrates having the primers immobilized thereon, and kept under the closed condition in a hybridization chamber for DNA microarray. Thermal denaturation was then allowed to proceed at 95° C. for 5 minutes, and a heat cycle of annealing and thermal denaturation under conditions of 50° C. for 3 minutes (annealing) and 95° C. for 1 minute (thermal denaturation) was repeated 15 times so as to elongate the DNA primers.

(Chromogenic Reaction)

After the elongation reaction, the solution for DNA elongation reaction was removed, the substrates were washed, a solution of streptoavidin-labeled alkali phosphatase was supplied to the surfaces of the substrates, allowed to stand at 37° C. for 30 minutes, the alkali phosphatase solution was removed, each substrate was washed, then supplied with a NBT/BICP solution, allowed to stand at 37° C. for 30 minutes, and the substrates were washed. Almost no coloration at the sites of spotting of the primers was visually observed on the aldehyde substrate, whereas coloration at the sites of spotting was clearly observed on the PMBN substrate.

Colored images of the sites of spotting of primers were captured by a CCD camera, and the captured digital data were processed by an image processing software (NIH image), and the degree of coloration was expressed by numerical values. Results are shown in Table 1.

TABLE 1

| Number of bases of primer | Degree of coloration (numerical expression) | |
|---|---|---|
| | PMBN substrate | Aldehyde substrate |
| 15 | 8480 | 362 |
| 20 | 5672 | 179 |
| 25 | 4300 | 119 |

Elongation of DNA chain was detected on the PMBN substrate treated on the surface thereof with a predetermined polymer substance, whereas almost no elongation of the DNA chain occurred and was not detected on the aldehyde substrate which is not treated on the surface thereof with the polymer substance.

The invention claimed is:

1. A method of detecting and quantifying a target DNA or RNA sequence in a sample which comprises
providing an insoluble carrier having on the surface thereof a polymer substance containing a first unit having a phosphorylcholine group and a second unit having a carboxylic acid-derived group having an electron-attractive substituent bound to a carbonyl group;
(a) immobilizing a primer for a given fragment of the target DNA or RNA sequence onto the surface of the insoluble carrier to give a primer-immobilized carrier;
(b) adding the sample, a polymerase selected from the group consisting of a DNA polymerase, an RNA polymerase, and a reverse transcriptase, and nucleotide monomers onto the primer-immobilized carrier, heating the sample to a thermal denaturation temperature for the given fragment of the target DNA or RNA sequence before or after adding the sample onto the primer-immobilized carrier, wherein the polymerase and the nucleotide monomers are heated to the thermal denaturation temperature before adding the polymerase and the nucleotide monomers onto the primer-immobilized carrier;
(c) incubating the primer and the sample at an annealing temperature which is predetermined for the given fragment; and
(d) adjusting the temperature to a predetermined temperature which will result in an elongated polynucleotide chain in the presence of the target DNA or RNA sequence; and
detecting the presence of the elongated polynucleotide chain using a chromogenic reagent which adsorbs to the elongated polynucleotide chain, and quantifying the amount of the elongated polynucleotide chain based on the degree of adsorption or the degree of coloration.

2. The method of claim 1, further comprising heating the primer-immobilized carrier, the sample, the polymerase, and the nucleotide monomers thereon the primer-immobilized carrier up to the thermal denaturation temperature.

3. The method of claim 1, wherein the nucleotide monomers are labeled with a label.

4. The method of claim 1, wherein the nucleotide monomers are labeled with biotin.

5. The method of claim 3, wherein the label is detectable with an oxidase or a reductase.

6. The method of claim 3, wherein label is detectable with a peroxidase or an alkali phosphatase.

7. The method of claim 1, wherein the predetermined temperature is between the annealing temperature and the thermal denaturation temperature.

8. The method of claim 1, wherein the primer is immobilized to the surface of the insoluble carrier through a covalent bond with a carboxylic acid-derived group.

9. The method of claim 1, wherein the polymer substance further contains a third unit having a butyl methacrylate group.

10. The method of claim 1, wherein the insoluble carrier further contains a second polymer substance containing a first unit having a phosphorylcholine group, and a third unit having a butyl methacrylate group.

11. The method of claim 1, wherein the insoluble carrier is composed of a plastic material.

* * * * *